(12) United States Patent
Wilder et al.

(10) Patent No.: US 6,716,241 B2
(45) Date of Patent: Apr. 6, 2004

(54) VENOUS VALVE AND GRAFT COMBINATION

(76) Inventors: John G. Wilder, 712 S. Gabriel Dr., Leander, TX (US) 78641; Aleta Tesar, 712 S. Gabriel Dr., Leander, TX (US) 78641

( * ) Notice: Subject to any disclaimer, the term of this patent is extended or adjusted under 35 U.S.C. 154(b) by 0 days.

(21) Appl. No.: 10/090,895

(22) Filed: Mar. 5, 2002

(65) Prior Publication Data

US 2003/0171802 A1 Sep. 11, 2003

(51) Int. Cl.[7] .................................................. A61F 2/06
(52) U.S. Cl. .................................. 623/1.24; 623/2.19
(58) Field of Search ............................ 623/1.24, 1.26, 623/2.11, 1.1, 2.19

(56) References Cited

U.S. PATENT DOCUMENTS

| | | | |
|---|---|---|---|
| 15,192 A | * 6/1856 | Peale | 137/844 |
| 5,358,518 A | 10/1994 | Camilli | 623/1.24 |
| 5,509,930 A | 4/1996 | Love | 623/1.24 |
| 5,545,215 A | * 8/1996 | Duran | 623/1.26 |
| 5,607,465 A | 3/1997 | Camilli | 623/1.24 |
| 5,957,949 A | 9/1999 | Leonhardt et al. | 606/194 |
| 6,126,686 A | 10/2000 | Badylak et al. | 623/1.24 |
| 6,168,614 B1 | 1/2001 | Andersen et al. | 623/1.24 |
| 6,241,763 B1 | 6/2001 | Drasler et al. | 623/1.24 |
| 6,299,637 B1 | 10/2001 | Shaolian et al. | 623/1.24 |
| 6,315,793 B1 | 11/2001 | Bokros et al. | 623/1.24 |
| 6,319,281 B1 | 11/2001 | Patel | 623/2.3 |
| 2002/0177894 A1 | * 11/2002 | Acosta et al. | 623/1.24 |

* cited by examiner

*Primary Examiner*—Bruce Snow
*Assistant Examiner*—Thomas J Sweet

(57) ABSTRACT

A synthetic venous valve and graft combination that exerts no radial force at the valve site is disclosed. The trilobed valve (11) is passively actuated by venous blood pressure changes. When open, the aperture for blood flow is approximately that of the original vein. The prosthesis is useful for replacing nonfunctioning venous valves in the human vasculature.

6 Claims, 2 Drawing Sheets

VENOUS VALVE AND GRAFT COMBINATION

CROSS-REFERENCE TO RELATED APPLICATIONS

Not applicable.

BACKGROUND—FIELD OF INVENTION

Our invention is a synthetic venous valve and graft combination, useful to replace a diseased, injured, or otherwise nonfunctioning venous valve in the human vasculature.

BACKGROUND—DISCUSSION OF PRIOR ART

Significant differences between the venous environment and the arterial environment should be considered when designing prosthetic venous valves. Much of vascular research and development to date has centered on the arterial system, as problems in this system tend to be life threatening. The most obvious difference between the two environments is the lower oxygen content of the venous blood. The lower oxygen content is a key factor in the exceedingly high propensity towards thrombus formation. Blood in the arterial system is moved rapidly and at high pressure by the heart. In contrast, blood is moved through the veins at slightly over half the arterial pressure (close to the measured systolic pressure) and more slowly. Blood flow rates in smaller veins can fall below one milliliter per second. Veins are surrounded by muscle that promotes blood flow during muscle tension/contraction. During muscular contraction of the vein, the change in vein diameter is large compared to arterial diameter change within a heartbeat. The venous system requires multiple valves to function whereas the arterial system lacks valves except in the heart. The normal function of venous valves is to direct the venous blood towards the heart by allowing only unidirectional flow. With the vein lumen contraction causing flow and the valves directing flow, a venous pressure is produced. It is important that the venous valves operate properly to prevent reverse flow or "reflux". Some venous valves may be required to actuate with a pressure change of less than 1 mm Hg. This is barely a differential of 1.5% of the normal venous pressure.

When, due to disease, injury, or congenital defect, valves do not properly operate, reflux can occur, causing blood to pool in the body extremities. Existing forms of pharmaceutical and surgical treatments for such venous disorders all have limitations. In some cases replacement valves are required to maintain a patient's ambulatory functions. Surgical techniques for valve replacement are complicated and delicate. Less invasive endovascular and percutaneous techniques are desirable and are known.

No currently available prosthetic valve fully addresses the special needs of the venous environment. An 1856 description of the design and operation of various "elastic valves" within tubes, which greatly predates all use of valves in mitral, aortic, arterial, or venous prostheses, is given by Peale (U.S. Pat. No. 15,192). Peale's description fails to clearly show how a trilobal valve can be formed inside a tube. One innovative invention (U.S. Pat. No. 6,241,763) describes forming a venous valve insitu by overlapping the vein wall and attaching it in place to form two tubular regions from one. A consequent increase in tissue bulk and decrease in vein lumen requires greater pressures and/or will move less blood volume. Both consequences encourage blood pooling. Other valve designs tend to be scaled-down versions of heart valves. These designs require a support wire, stent, annular "valve ring", or valve seat at the site of the valve, itself (see for examples U.S. Pat. Nos. 5,358,518; 5,607,465; 6,315,793; 6,319,281; 6,168,614; 6,299,637). All such devices place radially outward forces on the inner vein wall, causing radial stiffening. With a large percentage change in diameter during pulsation, any foreign object exerting radial stiffness causes local irritation to the vein wall. Foreign body irritation engenders neointimal hyperplasia, sclerosis, and associated thrombus formation. This is the major reason that stents, which have proven lifesaving in arteries, are not routinely used in veins.

Heart valves are often constructed of fixed biological tissues (notably U.S. Pat. Nos. 5,509,930 and 6,126,686). In the low flow and low oxygen venous environment, fixed tissues tend to calcify. Calcified and otherwise stiffened valves do not function well at low pressure differentials. Although some design features of the heart valve shown in U.S. Pat. No. 5,509,930 are desirable, the use of bulky layers of fixed biological tissue with folds and overlap seams prevent this invention from application as a suitable venous valve. The valve stent invention in U.S. Pat. No. 5,957,949 is a unibody wire stent covered with a graft to which a valve is permanently attached. The stated preferred valve is a treated bicuspid porcine valve and, although the stent design and construction are detailed, no design is provided for a synthetic valve.

SUMMARY

Our invention is a venous valve prosthesis designed specifically to meet the challenges of the venous environment: a synthetic valve and graft combination having a trilobal configuration in the actuating portion.

Objectives

With the foregoing in mind, it is an objective of our invention to design a streamlined synthetic venous valve and graft combination that applies no radial force on the vein wall at the valve site.

It is another objective of our invention to design a venous valve and graft combination that operates at pressure differentials approaching 1 mm Hg.

It is a further objective of our invention to provide a venous valve and graft combination having a small compressed bulk, and which can be flexibly tailored to meet the sizing, attachment, and delivery requirements of the patient.

Figure 1:
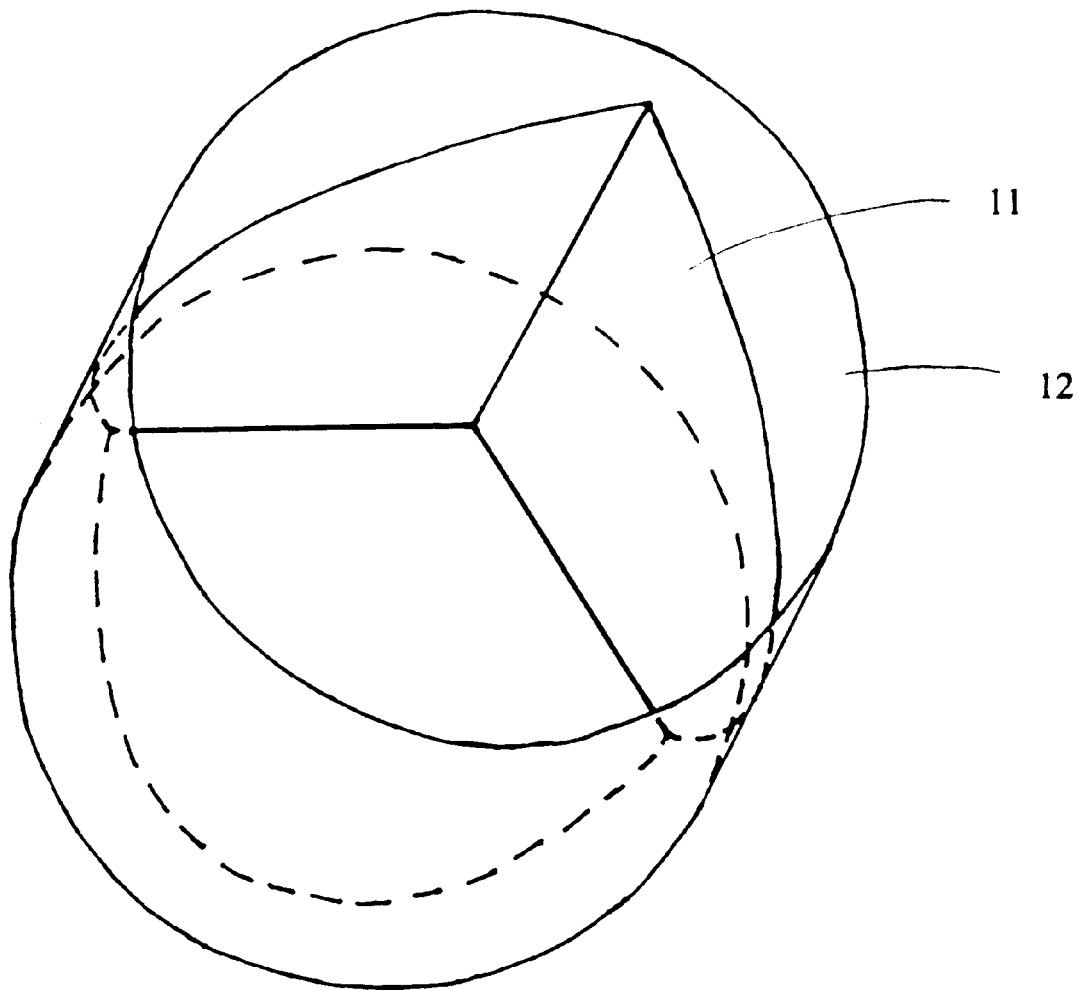
FIG. 1 shows a venous valve and graft combination with valve closed.

REFERENCE NUMERALS IN FIGURES 11 valve
12 graft
21 proximal end
22 distal end
25 warp insertion line
33 graft portion of inner tube
34 valve portion of inner tube

35 transition line
36 glued section of outer tube
37 section of outer tube without glue

DESCRIPTION—PREFERRED EMBODIMENT

Figure 2:
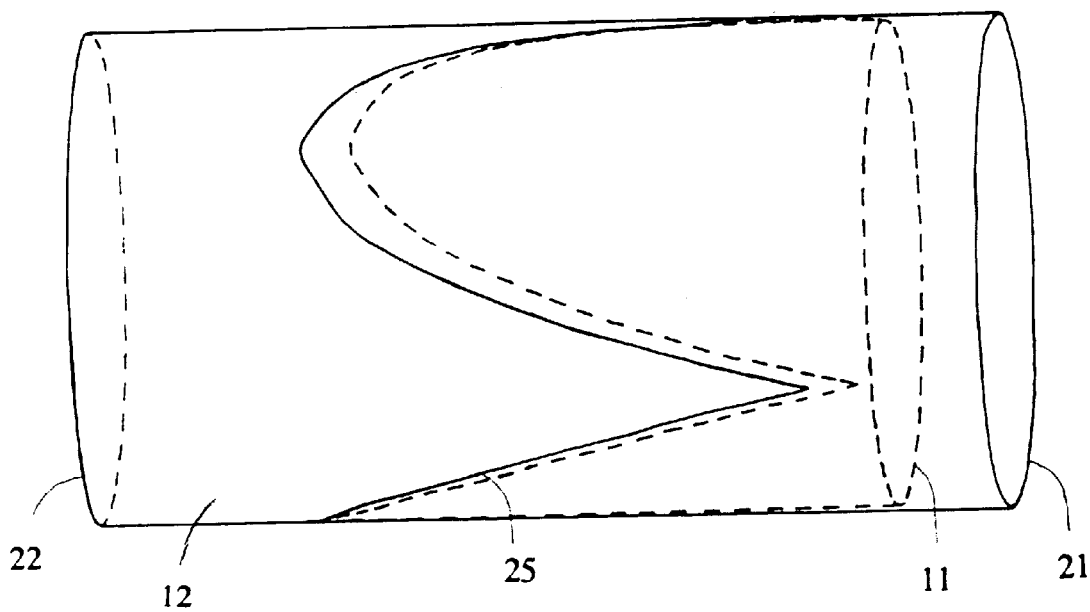
FIG. 2 shows a side view of a venous valve and graft combination with valve open.

A preferred embodiment of the valve and graft combination of the present invention is illustrated by FIGS. 1 and 2. The closed valve and graft combination shown in FIG. 1 demonstrates that the valve dimensions are related to the graft diameter. The streamlined profile when valve 11 is fully open (shown in FIG. 2) is a particularly desirable design feature. When the valve is fully open, the diameter for blood flow is essentially the graft 12 diameter minus two thicknesses of the valve material. The diameter of the graft is adjusted accordingly for the patient's vein (typically less than 10 mm). As the graft is held firmly against the inner vein wall by the venous blood pressure, the diameter available for blood flow becomes the original vein lumen minus four thicknesses of material. The lengths of the graft from the warp insertion line 25 (shown in FIG. 2) to the proximal end 21 and to the distal end 22 can also be adjusted to the patient's requirements. A taper can further be developed along the graft length, if necessary.

Essentially constructed of a short tube within a tube, the valve 11 (short tube) initiates and is connected to the graft (outer tube) along the warp insertion line 25 (see FIG. 2). This line traces three lobes, each lobe approximating a parabola, along the graft circumference. The circumference is Π (~3.1416) times the diameter, D. It follows that the distance along the graft between lobe apices is Π divided by 3 times D. The lobe length, between the lobe vertex and the lobe apex as measured parallel to the tube axis, must be at least 0.7 times D for proper valve closure. Although the valve will operate at larger lobe lengths (for example 2 times D), minimizing the lobe length also minimizes pooling of blood between the graft and the valve. The preferred lobe length is 0.74 times D. The edge length from the lobe apex to the trailing edge of the valve is similarly short, on the order of 0.1 to 0.5 times D. The preferred edge length is 0.2 times D, giving the total preferred valve length at its longest three lengths as 0.94 times D.

The valve and graft combination can be manufactured via specialized weaving techniques that form seamless tubes known to those in the field. This preferred embodiment demonstrates the valve and graft combination material as plain-woven of pre-stressed ultrahigh molecular weight polyethylene (UHMWPE) fiber. Woven polyethylene terephthalate (PET) textiles are widely used for arterial grafts. PET or similar hemocompatible fibers could also be used in this design. Woven textiles present unique advantages in compliance, high fatigue life, high strength, and breathability that offset inherent textile surface texture. To smooth surface texture, the finished woven prosthesis can be coated with a hemocompatible coating such as albumin. The exact textile thickness will be determined by the combination of warp and weft fiber diameters, and pic count of each; as available in medical grade fibers and known to those in the field, respectively. Typical thickness of the woven textile with low blood permeability is 0.06 mm.

The connection of the valve 11 to the graft 12 along the warp insertion line 25 is performed by interweaving a second short seamless tube inside the outer graft tube. For the trilobal actuating design shown in FIG. 2, a second warp fiber set is introduced on the loom into the outer tube during its weaving at warp and weft calculated to form three equivalent parabolas along the graft circumference. This second warp can be knotted on the outside of the graft and the length of free warp fiber ends can form a short fringe. Alternatively, the second warp ends can also be woven into the graft or valve textile. The valve is woven to desired finished length inside the graft. A fringe can be formed on the trailing edge of the valve, which may enhance the hydrodynamic properties of the valve.

Following standard cleaning and sterilization procedures known to those in the field, the graft and valve combination as so manufactured can be surgically implanted and attached to the vein lumen via sutures.

DESCRIPTION—ALTERNATIVE EMBODIMENTS

Figure 3:
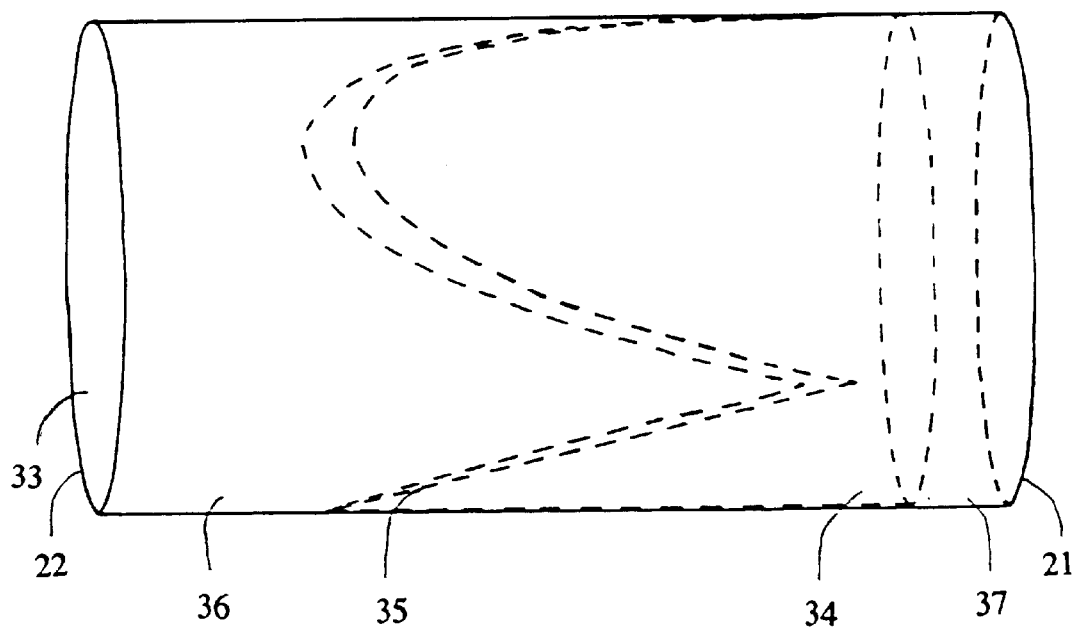
FIG. 3 shows a side view of another venous valve and graft combination made of two glued tubes.

There are alternative manufacturing possibilities with regard to forming a venous valve and graft combination with the desired design objectives. A valve and graft combination comprising two seamless tubes of expanded polytetrafluoroethylene (ePTFE) are shown in FIG. 3 with one tube inside the other tube. Both tubes have essentially the same diameter. The inner tube and outer tube are glued together from the distal end 22 to the transition line 35. An available glue for this application is fluorinated ethylene propylene. The transition line 35 is the trilobal pattern traversing the circumference of the valve and graft combination as described previously. The glued section of outer tube 36 and the graft portion of inner tube 33 form one part of graft 12. The section of outer tube without glue 37 forms the second part of graft 12, extending to the proximal end 21. The valve portion of inner tube 34, which is not glued, is identical to valve 11.

A further refinement to this design can include endothelial cell seeding of the ePTFE surface to reduce the possibility of thrombus formation. Endothelial cell seeding is a developing technology known to those practiced in the field.

As medical grade ePTFE tubes are available with wall thicknesses of around 0.04 mm, this valve and graft combination will exhibit a low bulk profile and can be endovascularly delivered into the patient's vein via a standard catheter. One attachment option is cuffs at both the distal end 22 and the proximal end 21. The cuffs would surround the outer surface of the graft 12 for a short length and would provide a temporary biocompatible adhesive and an endothelial ingrowth surface. Biocompatible adhesives that are triggered by contact with blood and appropriate ingrowth surface features are known. Further specialized attachment options are available, as may be called for by varying venous conditions. These include, but are not limited to, various technologies such as staples, hooks and/or barbs, expandable cuff stents, and permanent graft-to-tissue adhesives.

Operation

A prosthetic venous valve replaces a diseased, injured, or otherwise nonfunctioning venous valve in the human vasculature. A venous graft lines the lumen of a vein serving as a blood conduit. Our venous valve and graft combination provides both functions. The manufactured venous valve and graft combination can be delivered via a surgical, endovascular, or percutaneous procedure known to those practiced in the field. Numerous specialized attachment options are available. Once positioned in a vein and filled with blood, the graft 12 will remain patent and in contact with the vein wall. It may cover the site of the original nonfunctioning valve, reducing calcification and stenosis at that site. The graft statically supports the dynamic valve 11, eliminating the need for a stent in contact with the valve. The trilobed valve reacts to local venous pressure change, opening during distally higher pressure and closing during proximally higher pressure. At closure, the trailing edge of the valve contacts within the lumen, effectively closing the lumen.

Advantages

From the description, a number of advantages of our synthetic venous valve and graft combination become evident:

(a) The valve and graft combination exerts no radial forces on the vein wall at the valve site. Inherent in the design is compliant material. Both features minimize irritation to the vein tissue.

(b) The prosthetic valve and graft combination provide all three desirable flow features: the valve actuates at pressure differentials that approach 1 mm Hg; actuation is rapid when a venous pressure differential develops; and the blood flow channel diameter approximates the vein lumen diameter when the valve is open.

(c) The valve and graft combination can be manufactured from readily available synthetic materials that are approved for vascular prostheses.

(d) The compressed size of the valve and graft combination presents a low profile, useful for providing a choice between percutaneous, endovascular, and standard surgical insertion.

(e) The valve and graft combination can be easily sized to special patient requirements.

Conclusion, Ramifications, and Scope

Accordingly, the reader will see that the synthetic valve and graft combination of this invention can be used as a venous valve prosthesis. The valve and graft combination design produces no radial forces at the valve site, actuates at blood pressure differentials approaching 1 mm Hg, and can easily be tailored to meet the sizing requirements of the patient. Furthermore, the new valve and graft combination design has additional advantages in that the materials required for manufacture are available;

all of the materials required for manufacture are compliant;

the streamlined profile of the prosthesis may cause this prosthesis to be favored for use in small diameter veins;

the small compressed bulk of this prosthesis will allow delivery by endovascular procedures as well as surgical procedures.

Although the description above contains specificities, these should not be construed as limiting the scope of the invention but as merely providing illustrations of some of the presently preferred embodiments of this invention. The scope of this invention should be determined by the appended claims and their legal equivalents.

We claim:

1. An implantable, fully pliable, venous prosthesis comprising:
   (a) a synthetic, biocompatible, longitudinally seamless, outer tube that is the diameter of the lumen of a diseased, injured, or otherwise nonfunctioning section of human vein,
   (b) a synthetic, biocompatible, longitudinally seamless, inner tube of essentially the same diameter as the outer tube,
   (c) a means for securing said inner tube inside said outer tube in a line along the circumference that forms three equivalent and approximately parabolic sections, with the juncture of said inner tube and said outer tube streamlined on surfaces in contact with flowing blood, whereby said parabolic sections are supported at said line along the circumference, and whereby said outer tube is conforming to the natural vein contours and movement, and whereby blood is allowed to flow only in one direction within said prosthesis.

2. The prosthesis of claim 1 wherein said three parabolic sections form three actuating lobes of a trilobal valve, whereby said three lobes are open, lie flush against said outer tube, with full lumenal aperture when distal pressure, the pressure of blood arriving to the graft from the heart, is greater than proximal pressure, the pressure of blood departing from the graft to the heart, and fully closed, said three lobes contact each other in the center of the lumen, when these pressure conditions reverse.

3. The prosthesis of claim 2 wherein said outer tube having diameter, D, said inner tube having a length, L, of greater than 0.7D to 3.0D, said outer tube having a length of at least 1.0D.

4. The prosthesis of claim 3 wherein said outer tube can be lengthened as needed to cover said diseased, injured, or otherwise non-functioning section of human vein.

5. The prosthesis of claim 4 exhibiting a radially compressed size of less than 12 French, 4 mm diameter, for delivery.

6. The prosthesis of claim 5 employing a means of attachment to said vein at each end of said outer tube, whereby said prosthesis is held stationary where delivered within said diseased, injured, or otherwise non-functioning section of human vein.

* * * * *